US012678161B2

(12) United States Patent
Ding et al.

(10) Patent No.: US 12,678,161 B2
(45) Date of Patent: Jul. 14, 2026

(54) SURGICAL STAPLE CARTRIDGE WITH INSTALLATION POKA-YOKE FEATURES

(71) Applicant: Cilag GmbH International, Zug (CH)

(72) Inventors: Sheng Ding, Shanghai (CN); Jie Zhang, Shanghai (CN); Mengli Yang, Shanghai (CN); Junjie Wang, Shanghai (CN)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/851,261

(22) PCT Filed: Apr. 5, 2023

(86) PCT No.: PCT/IB2023/053483
§ 371 (c)(1),
(2) Date: Sep. 26, 2024

(87) PCT Pub. No.: WO2023/194935
PCT Pub. Date: Oct. 12, 2023

(65) Prior Publication Data
US 2025/0213250 A1      Jul. 3, 2025

(30) Foreign Application Priority Data
Apr. 8, 2022    (CN) .......................... 202210369715.9

(51) Int. Cl.
*A61B 17/072*      (2006.01)
*A61B 90/00*      (2016.01)

(52) U.S. Cl.
CPC ........ *A61B 17/07207* (2013.01); *A61B 90/08* (2016.02); *A61B 2017/07271* (2013.01); *A61B 2090/0808* (2016.02)

(58) Field of Classification Search
CPC .............................. A61B 17/072; A61B 90/08
See application file for complete search history.

(56) References Cited

U.S. PATENT DOCUMENTS

| 4,354,628 A | 10/1982 | Green |
| 4,527,724 A | 7/1985 | Chow et al. |
| | (Continued) | |

FOREIGN PATENT DOCUMENTS

| CN | 102835983 B | 8/2016 |
| EP | 0537572 B1 | 6/1999 |
| | (Continued) | |

OTHER PUBLICATIONS

International Search report and Written Opinion dated Jul. 14, 2023, for International Application No. PCT/IB2023/053483, 12 pages.
(Continued)

*Primary Examiner* — Nathaniel C Chukwurah
(74) *Attorney, Agent, or Firm* — FBT Gibbons LLP

(57) ABSTRACT

A surgical staple cartridge includes installation poka-yoke features. The surgical staple cartridge is configured to be installed between a pair of closure plates of a surgical instrument. The closure plates are configured to push the surgical staple cartridge towards a staple anvil portion of the surgical instrument to clamp tissue between the surgical staple cartridge and the staple anvil portion. The surgical staple cartridge includes two opposite side walls extending in a longitudinal direction parallel to an installation direction of the surgical staple cartridge. A protrusion and/or a slot are provided on an outer surface of at least one of the side walls. The protrusion as well as the slot are configured to cooperate with corresponding features on the closure plates, so as to prevent an inappropriate installation of the surgical staple cartridge.

20 Claims, 17 Drawing Sheets

(56)                References Cited

U.S. PATENT DOCUMENTS

| | | | |
|---|---|---|---|
| 4,568,009 A | | 2/1986 | Green |
| 4,573,622 A | | 3/1986 | Green et al. |
| 4,585,153 A | | 4/1986 | Failla |
| 4,715,520 A | | 12/1987 | Roehr et al. |
| 4,805,523 A | | 2/1989 | Stuckey et al. |
| 4,805,823 A | | 2/1989 | Rothfuss |
| 4,848,637 A | | 7/1989 | Pruitt |
| 4,930,503 A | | 6/1990 | Pruitt |
| 5,439,155 A | * | 8/1995 | Viola .................. A61B 17/072 227/176.1 |
| 5,462,215 A | * | 10/1995 | Viola .................. A61B 17/072 227/176.1 |
| 5,547,117 A | | 8/1996 | Hamblin et al. |
| 5,641,111 A | | 6/1997 | Ahrens et al. |
| 5,810,240 A | | 9/1998 | Robertson |
| 5,919,198 A | | 7/1999 | Graves et al. |
| 6,805,273 B2 | | 10/2004 | Bilotti et al. |
| 6,817,508 B1 | | 11/2004 | Racenet et al. |
| 7,735,704 B2 | | 6/2010 | Bilotti |
| 8,328,064 B2 | | 12/2012 | Racenet et al. |
| 11,202,628 B2 | | 12/2021 | Posey et al. |
| 2004/0084505 A1 | | 5/2004 | Bilotti et al. |
| 2005/0139629 A1 | | 6/2005 | Schwemberger et al. |
| 2011/0226837 A1 | | 9/2011 | Baxter, III et al. |
| 2013/0206813 A1 | | 8/2013 | Nalagatla |
| 2015/0119904 A1 | | 4/2015 | Ji et al. |
| 2017/0281177 A1 | | 10/2017 | Harris et al. |
| 2020/0205810 A1 | | 7/2020 | Posey et al. |
| 2020/0205811 A1 | | 7/2020 | Posey et al. |
| 2020/0337699 A1 | | 10/2020 | Rector et al. |
| 2020/0337700 A1 | | 10/2020 | Hontz et al. |
| 2021/0186495 A1 | | 6/2021 | Shelton, IV et al. |
| 2022/0000479 A1 | | 1/2022 | Shelton, IV et al. |
| 2022/0142641 A1 | | 5/2022 | Wang |
| 2024/0225642 A1 | | 7/2024 | Ren et al. |
| 2025/0049436 A1 | | 2/2025 | Wang |
| 2025/0195065 A1 | | 6/2025 | Yang et al. |
| 2025/0204912 A1 | | 6/2025 | Yang et al. |
| 2025/0213248 A1 | | 7/2025 | Zhang et al. |
| 2025/0213250 A1 | | 7/2025 | Ding et al. |
| 2025/0228559 A1 | | 7/2025 | Ding et al. |
| 2025/0255605 A1 | | 8/2025 | Yang et al. |

FOREIGN PATENT DOCUMENTS

| | | | |
|---|---|---|---|
| EP | 1552791 | B1 | 6/2009 |
| EP | 1550411 | B1 | 7/2009 |
| EP | 2368503 | A1 | 9/2011 |
| EP | 3476310 | A1 | 5/2019 |
| EP | 3225179 | B1 | 4/2020 |
| EP | 3673826 | A1 | 7/2020 |
| EP | 3730070 | A1 | 10/2020 |
| EP | 3730069 | B1 | 7/2023 |
| EP | 3730068 | B1 | 9/2023 |
| EP | 3636166 | B1 | 3/2024 |
| WO | 2021/168704 | A1 | 9/2021 |
| WO | 2021/168726 | A1 | 9/2021 |

OTHER PUBLICATIONS

International Search Report and Written Opinion dated Jul. 4, 2023 for Application No. PCT/IB2023/053467, 9 pages.
International Search Report and Written Opinion dated Jul. 12, 2023 for Application No. PCT/IB2023/053469, 9 pages.
International Search Report and Written Opinion dated Jul. 21, 2023 for Application No. PCT/IB2023/053476, 9 pages.
International Search Report and Written Opinion dated Jun. 29, 2023 for Application No. PCT/IB2023/053477, 10 pages.
International Search Report and Written Opinion dated Jul. 5, 2023 for Application No. PCT/IB2023/053478, 9 pages.
International Search Report and Written Opinion dated Jul. 5, 2023 for Application No. PCT/IB2023/053481, 10 pages.
International Search Report and Written Opinion dated Jul. 9, 2025, for International Application No. PCT/EP2025/061136, 9 pages.

* cited by examiner

23

33

100

SURGICAL STAPLE CARTRIDGE WITH INSTALLATION POKA-YOKE FEATURES

FIELD

The present disclosure relates to the field of surgical instruments, in particular, to the field of surgical staplers/anastomats.

BACKGROUND

A surgical stapler/anastomat is often used to deploy staples into tissue for reducing or eliminating tissue bleeding, for example, it is necessary to seal the tissue as the tissue being cut in order to promote healing. A surgical stapler/anastomat (such as a linear stapler/anastomat, a right-angle stapler/anastomat) may comprise an end effector assembly having a staple cartridge portion and a staple anvil portion, the end effector assembly is configured to secure the tissue between the staple cartridge portion and the staple anvil portion, wherein the staple cartridge portion comprises a replaceable staple cartridge configured to removably store surgical staples therein, and the staple anvil portion comprises staple forming pockets for forming the staples. Such surgical stapler/anastomat generally comprises a closure system that moves one of the staple cartridge portion and the staple anvil portion relative to the other, and a staple driver for firing the staples.

During use, the staple cartridge portion and the staple anvil portion of the end effector assembly of the surgical stapler/anastomat are closed to form a close configuration, in order to capture the tissue between the staple cartridge portion and the staple anvil portion. Then, the staple driver pushes the staples to deploy from the staple cartridge, pass through the tissue, and to be formed against the staple forming pockets of the staple anvil portion, so as to seal tissue layers together. The staples are usually deployed in form of several staple lines or staple rows in order to secure the tissue layers together more reliably. The end effector assembly may comprise or not comprise a cutting member that can be advanced between the staple lines in order to cut the tissue after the tissue layers have been sealed together.

The staple cartridges and the surgical instruments usually come in a variety of models for different tissue sites and situations. A certain model of the staple cartridge may be used for one or more models of surgical instruments. In the case that an incompatible staple cartridge is installed in the surgical instrument or a compatible staple cartridge is installed in the surgical instrument in an incorrect direction, it may affect the tissue sealing quality, cause the surgical instrument to malfunction, or even damage the surgical instrument and staple cartridge.

Therefore, a staple cartridge with installation poka-yoke function is needed to avoid the above situation.

SUMMARY

The present disclosure provides a surgical staple cartridge with installation poka-yoke features, the poka-yoke features are configured to prevent an incorrect model of staple cartridge from being installed into a surgical instrument or a correct model of staple cartridge from being installed into the surgical instrument along an incorrect direction, and to indicate a user to install a correct model of staple cartridge along a correct installation direction. Moreover, in certain models of surgical instruments, a staple driver of the surgical instrument is locked by a lock device, which can be unlocked by the staple cartridge installed in place. Therefore, when the surgical staple cartridge with the installation poka-yoke features provided by the present disclosure is installed in an incompatible surgical instrument, the lock device will not be unlocked, so that the surgical instrument will not be able to fire.

In one aspect, the present disclosure provides a surgical staple cartridge configured to be removably installed between a pair of closure plates of a surgical instrument, the closure plates are configured to push the surgical staple cartridge towards a staple anvil portion of the surgical instrument to clamp tissue between the surgical staple cartridge and the staple anvil portion, wherein the surgical staple cartridge comprises: a first side wall extending along a longitudinal direction parallel to an installation direction of the surgical staple cartridge, a first protrusion is provided on an outer surface of the first side wall at a position adjacent to a top end of the first side wall; a second side wall arranged in parallel and opposite to the first side wall; wherein the first protrusion is configured to match with a first notch at a top end of a first closure plate to guide the surgical staple cartridge to be correctly installed.

According to a preferred embodiment of the present disclosure, the first protrusion has a substantially triangular profile, and wherein a vertex of the triangular profile faces towards the installation direction of the surgical staple cartridge.

According to a preferred embodiment of the present disclosure, the first protrusion has a substantially arc profile or trapezoidal profile, and wherein a tapered end of the arc profile or the trapezoidal profile faces towards the installation direction of the surgical staple cartridge.

According to a preferred embodiment of the present disclosure, a profile of the first notch of the first closure plate is substantially matched with that of the first protrusion.

According to a preferred embodiment of the present disclosure, a recess area is provided in the first protrusion, and a profile of the recess area is designed to indicate the installation direction of the surgical staple cartridge.

According to a preferred embodiment of the present disclosure, the profile of the recess area is substantially the same as the profile of the first protrusion.

According to a preferred embodiment of the present disclosure, a second protrusion is provided on an outer surface of the second side wall at a position adjacent to a top end of the second side wall, and wherein the second protrusion is configured to match with a second notch at a top end of a second closure plate of the surgical instrument to guide the surgical staple cartridge to be correctly installed.

According to a preferred embodiment of the present disclosure, the second protrusion has a substantially triangular profile, and wherein a vertex of the triangular profile faces towards the installation direction of the surgical staple cartridge.

According to a preferred embodiment of the present disclosure, the second protrusion has a substantially arc profile or trapezoidal profile, and wherein a tapered end of the arc profile or the trapezoidal profile faces towards the installation direction of the surgical staple cartridge.

According to a preferred embodiment of the present disclosure, a profile of the second notch of the second closure plate is substantially matched with that of the second protrusion.

According to a preferred embodiment of the present disclosure, a recess area is provided in the second protrusion, and a profile of the recess area is designed to indicate the installation direction of the surgical staple cartridge.

According to a preferred embodiment of the present disclosure, the profile of the recess area is substantially the same as that of the second protrusion.

According to a preferred embodiment of the present disclosure, the first protrusion and the second protrusion have same or different profiles.

According to a preferred embodiment of the present disclosure, a first slot extending in the longitudinal direction is further provided on the outer surface of the first side wall, and the first slot is configured to receive one or more ribs provided on an inner surface of the first closure plate.

According to a preferred embodiment of the present disclosure, a second slot extending in the longitudinal direction is further provided on the outer surface of the second side wall, and the second slot is configured to receive one or more ribs provided on an inner surface of the second closure plate.

According to a preferred embodiment of the present disclosure, the first slot and the second slot are asymmetrically arranged on the lateral sides of the surgical staple cartridge.

According to a preferred embodiment of the present disclosure, a first slot extending in the longitudinal direction is further provided on the outer surface of the first side wall, and the first slot includes a first partial slot adjacent to the top end of the first side wall and a second partial slot adjacent to a bottom end of the first side wall, the second partial slot being wider than the first partial slot.

According to a preferred embodiment of the present disclosure, a side of the second partial slot is aligned with a same side of the first partial slot, and when the surgical staple cartridge is installed between the first closure plate and the second closure plate along the installation direction, the first partial slot is configured to receive one or more first ribs provided on an inner surface of the first closure plate, and the second partial slot is configured to receive one or more second ribs provided on the inner surface of the first closure plate, the one or more second ribs being staggered from the one or more first ribs.

According to a preferred embodiment of the present disclosure, the first slot further comprises a flared section located at a bottom end of the second partial slot.

According to a preferred embodiment of the present disclosure, a second slot extending in the longitudinal direction is further provided on the outer surface of the second side wall, and the second slot includes a third partial slot adjacent to the top end of the second side wall and a fourth partial slot adjacent to a bottom end of the second side wall, the fourth partial slot being wider than the third partial slot.

According to a preferred embodiment of the present disclosure, a side of the fourth partial slot is aligned with a same side of the third partial slot, and when the surgical staple cartridge is installed between the first closure plate and the second closure plate in the installation direction, the third partial slot is configured to receive one or more third ribs provided on an inner surface of the second closure plate, and the fourth partial slot is configured to receive one or more fourth ribs provided on the inner surface of the second closure plate, the one or more fourth ribs being staggered from the one or more third ribs.

According to a preferred embodiment of the present disclosure, the second slot further comprises a flared section located at a bottom end of the fourth partial slot.

In another aspect, the present disclosure further provides a closure member for a surgical instrument, the closure member is configured to removably hold a surgical staple cartridge and push the surgical staple cartridge towards a staple anvil portion of the surgical instrument to clamp tissue between the surgical staple cartridge and the staple anvil portion, wherein the closure member comprises a first closure plate and a second closure plate arranged opposite to the first closure plate, wherein the surgical staple cartridge is configured to be removably installed between the first closure plate and the second closure plate, and wherein a top end of the first closure plate is provided with a first notch for receiving a first protrusion on a first side wall of the surgical staple cartridge.

According to a preferred embodiment of the present disclosure, the first notch of the first closure plate has a substantially triangular profile, and wherein a vertex of the triangular profile faces towards an installation direction of the surgical staple cartridge.

According to a preferred embodiment of the present disclosure, the first notch of the first closure plate has a substantially arc profile or trapezoidal profile, and wherein a tapered end of the arc profile or the trapezoidal profile faces towards an installation direction of the surgical staple cartridge.

According to a preferred embodiment of the present disclosure, a top end of the second closure plate is provided with a second notch for receiving a second protrusion on a second side wall of the surgical staple cartridge opposite to the first side wall.

According to a preferred embodiment of the present disclosure, the second notch of the second closure plate has a substantially triangular profile, and wherein a vertex of the triangular profile faces towards an installation direction of the surgical staple cartridge.

According to a preferred embodiment of the present disclosure, the second notch of the second closure plate has a substantially arc profile or trapezoidal profile, and wherein a tapered end of the arc profile or the trapezoidal profile faces towards an installation direction of the surgical staple cartridge.

According to a preferred embodiment of the present disclosure, the first notch and the second notch have same or different profiles.

According to a preferred embodiment of the present disclosure, an inner surface of the first closure plate is provided with one or more first ribs extending along an installation direction of the surgical staple cartridge.

According to a preferred embodiment of the present disclosure, an inner surface of the second closure plate is provided with one or more third ribs extending along the installation direction of the surgical staple cartridge.

According to a preferred embodiment of the present disclosure, the first ribs and the third ribs are asymmetrically arranged on the inner surfaces of the closure member with respect to each other.

According to a preferred embodiment of the present disclosure, the inner surface of the first closure plate is further provided with one or more second ribs extending along the installation direction of the surgical staple cartridge, the one or more second ribs being staggered with the one or more first ribs.

According to a preferred embodiment of the present disclosure, the inner surface of the second closure plate is further provided with one or more fourth ribs extending along the installation direction of the surgical staple cartridge, the one or more fourth ribs being staggered with the one or more third ribs.

In a further aspect, the present disclosure provides a surgical instrument, which comprises the staple cartridge according to the foregoing embodiments and the closure member according to the foregoing embodiments.

BRIEF DESCRIPTION OF THE DRAWINGS

The present disclosure and its features and advantages will be better understood with reference to the following description of exemplary embodiments of the present disclosure in conjunction with the accompanying drawings. In the following description and drawings, similar components are indicated with similar reference signs. The figures are not necessarily drawn to scale, and for the sake of clarity and conciseness, some parts may be omitted, and some figures may be drawn in an exaggerated or sketchy way.

DETAILED DESCRIPTION OF EMBODIMENTS

Next, exemplary embodiments of the present disclosure will be described in detail with reference to the accompanying drawings. Described herein are merely exemplary embodiments in accordance with the present disclosure, and those skilled in the art will envisage other ways to implement the present disclosure on the basis of the exemplary embodiments described herein, which also fall within the scope of the present disclosure.

Figure 2:
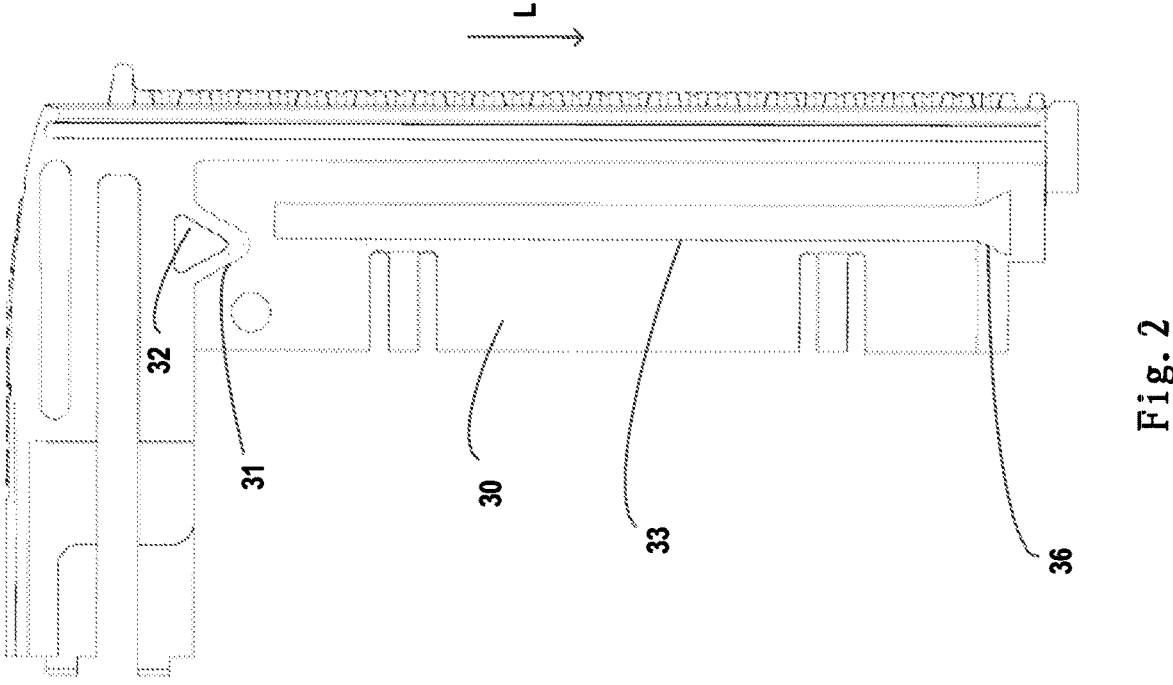
FIG. 2 exemplarily shows another side of the surgical staple cartridge shown in FIG. 1.
Figure 1:
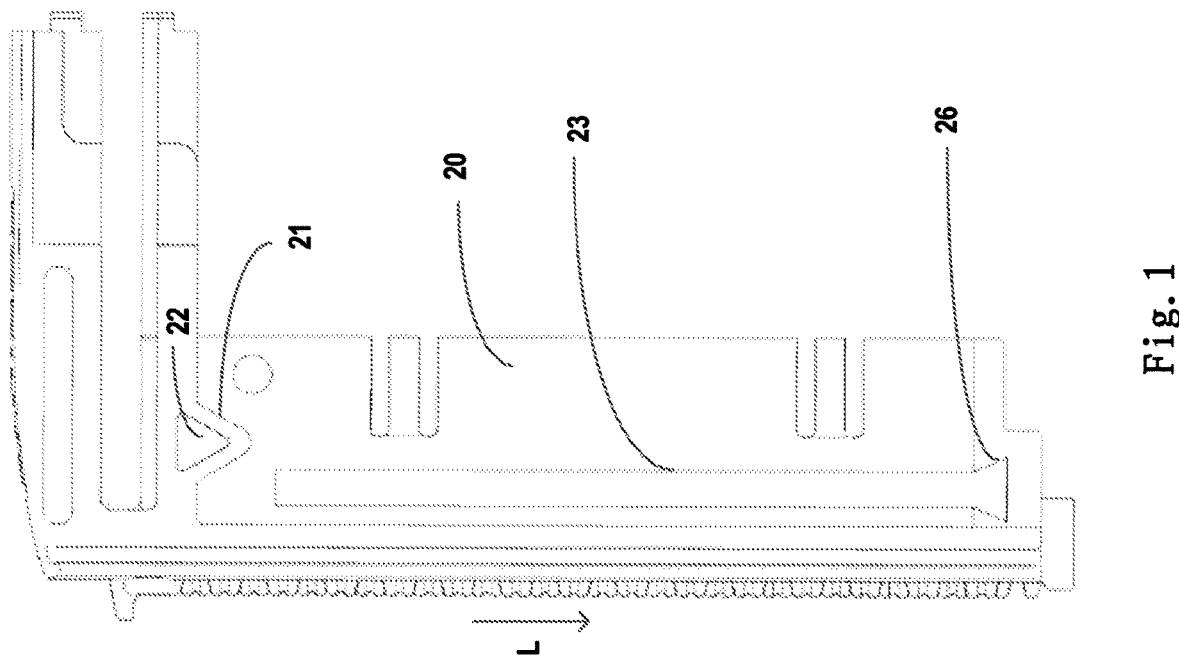
FIG. 1 exemplarily shows one side of a surgical staple cartridge according to a preferred embodiment of the present disclosure.
Figure 3:
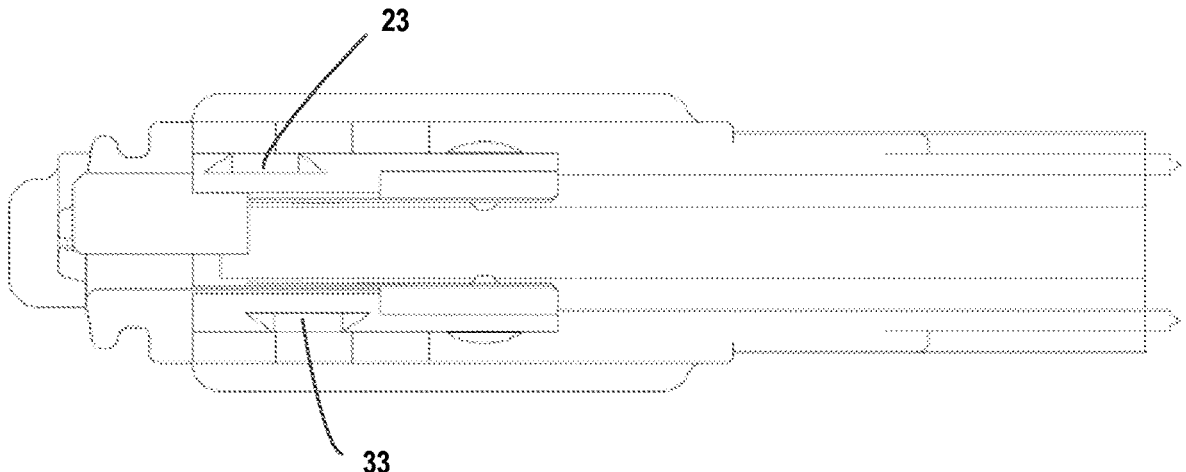
FIG. 3 exemplarily shows a bottom view of the surgical staple cartridge shown in FIG. 1.

FIG. 1 to FIG. 3 exemplarily show a surgical staple cartridge according to one embodiment of the present disclosure, wherein the surgical staple cartridge comprises side walls 20, 30 which extend along a longitudinal direction L (an installation direction of the staple cartridge in a surgical instrument), and the two side walls 20, 30 are arranged in parallel and opposite to each other. A first protrusion 21 is provided on an outer surface of the first side wall 20 at a position adjacent to a top end of the first side wall 20, the first protrusion 21 is used to match with a notch at a top end of a first closure plate of the surgical instrument, in order to guide the surgical staple cartridge to be correctly installed, while preventing an incorrect model of surgical staple cartridge from being installed into the surgical instrument.

Referring to FIG. 2, a second protrusion 31 is provided on an outer surface of the second side wall 30 at a position adjacent to a top end of the second side wall 30, the second protrusion 31 is used to match with a notch at a top end of a second closure plate of the surgical instrument, in order to guide the surgical staple cartridge to be correctly installed, while preventing an incorrect model of surgical staple cartridge from being installed into the surgical instrument.

The protrusions 21, 31 shown in the figures are of generally inverted triangular profiles, wherein a vertex of the triangular profile faces towards the installation direction of the staple cartridge, which is helpful to guide the staple cartridge to be correctly installed in the surgical instrument. The first protrusion 21 is further provided with a recess area 22 having substantially the same profile as that of the first protrusion 21, and the recess area 22 may be used to indicate the installation direction of the surgical staple cartridge. Therefore, the recess area 22 may have other profiles as long as it can indicate the installation direction of the surgical staple cartridge for the user. A similar recess area 32 is provided in the second protrusion 31.

Further, the surgical staple cartridge of the present disclosure may further comprise slots 23, 33 respectively positioned on the outer surfaces of the two side walls 20, 30. The slots 23, 33 are respectively positioned below the protrusions 22, 32, and extend along the installation direction L of the staple cartridge. The slots 23, 33 are asymmetrically arranged on the lateral sides of the surgical staple cartridge with respect to each other, and as shown in FIG. 3, the slot 23 is more distally positioned (i.e., away from an operator) than the slot 33. Of course, in an alternative embodiment, the slot 23 may be more proximally positioned (that is, close to the operator) than the slot 33. The slot 23 and the slot 33 may also be symmetrically arranged with respect to each other on lateral sides of the surgical staple cartridge. The slots may cooperate with ribs on inner sides of the closure plates of the surgical instrument, thus enabling the ribs to be received in the slots, which on one hand may be used to prevent the staple cartridge from being installed in an incompatible model of surgical instrument (that is, the position of the ribs on the inner side of the closure plates of the surgical instrument does not match with the position of the slots on the staple cartridge), and on the other hand, may be used to assist the closure plate to push the staple cartridge.

Figure 4:
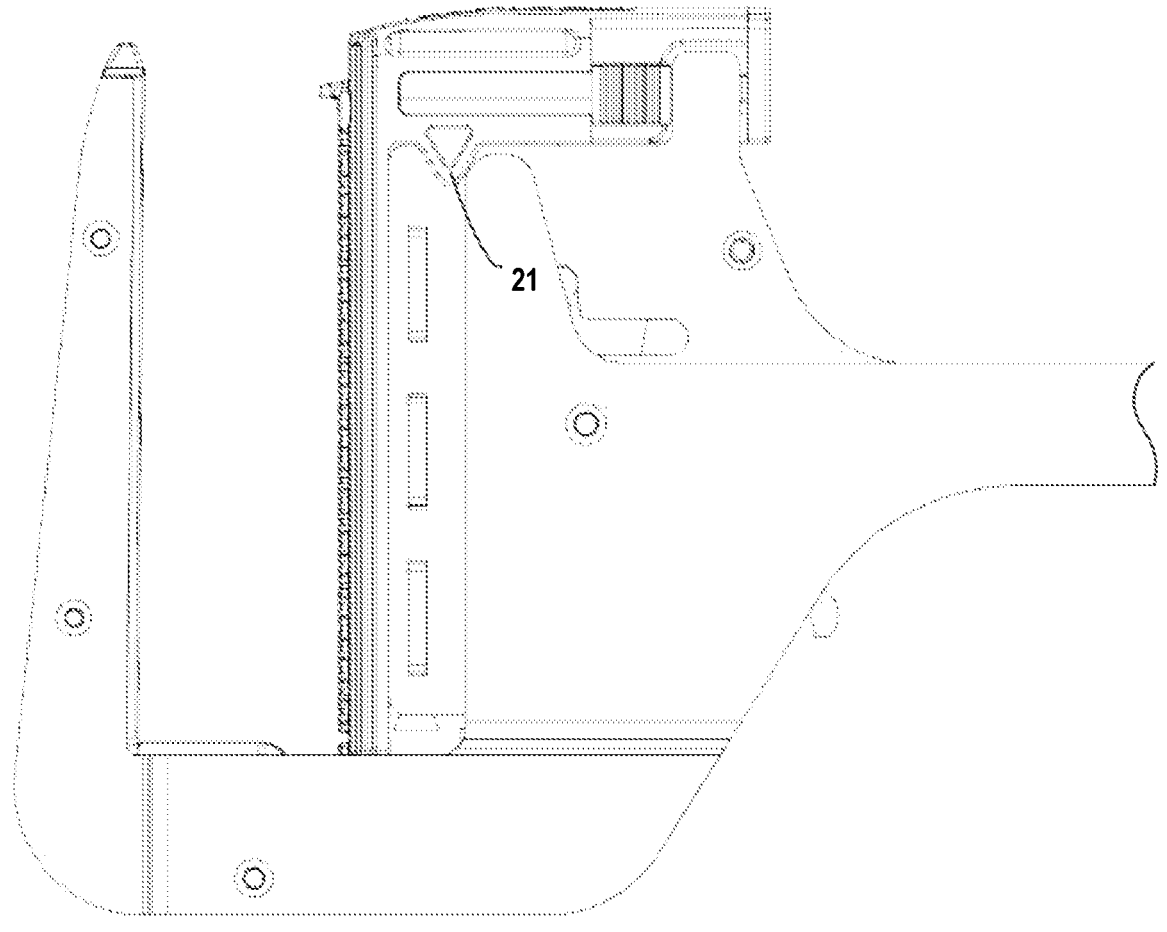
FIG. 4 exemplarily shows a side view of the surgical staple cartridge of FIG. 1 when installed in a surgical stapler according to the present disclosure.
Figure 5:
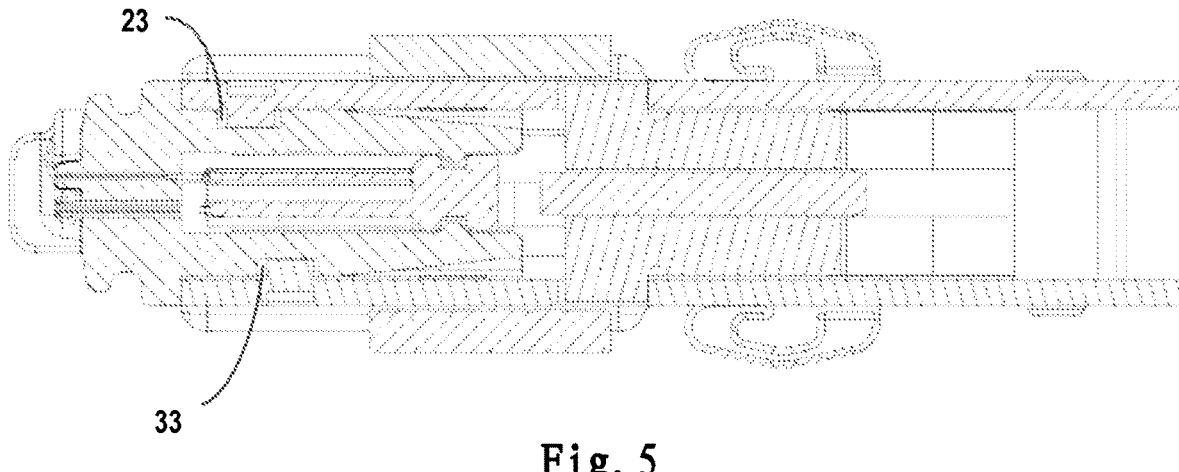
FIG. 5 is an enlarged partial cross-sectional view of the surgical stapler shown in FIG. 4 with the surgical staple cartridge installed.

FIG. 4 and FIG. 5 show that the staple cartridge of FIG. 1 is installed in a compatible model of surgical instrument, wherein the protrusions 21, 31 are respectively received in the notches of the corresponding closure plates, and the ribs on the inner sides of the two closure plates of the surgical instrument are slidably received in the corresponding slots 23, 33.

In some embodiments, a mis-installation of the staple cartridge may further be prevented by changing positions of the protrusions and the notches of the closure plates described above. For example, when the protrusions 21, 31 and the notches of the corresponding closure plates are positioned to a more proximal position along a proximal direction (that is, more close to the operator, a right direction shown in FIG. 4), a staple cartridge with the protrusions arranged at more distal positions will not be able to install, because distal ends of the closure plates will abut against or interfere with corresponding portions of the staple cartridge, causing that the protrusions of the staple cartridge cannot align with and be received in the notches of the closure plates which are proximally positioned relative to the protrusions.

In some models of surgical instruments, the surgical instrument comprises a lock device for locking a staple driver, wherein the lock device may be unlocked by the staple cartridge installed in place, for example, by engagement between the lock device and the bottom portion of the staple cartridge. Therefore, when the surgical staple cartridge with installation poka-yoke features provided by the present disclosure is installed in an incompatible surgical instrument, the lock device will not be unlocked because the staple cartridge can't be installed in place along the installation direction, so that the surgical instrument cannot fire.

In a further preferred embodiment, open tip ends of the slots 23, 33 may further have funnel-shaped flared sections 26, 36 to assist the alignment of the slots with the ribs, so as to facilitate the installation of the staple cartridge.

Figure 6:
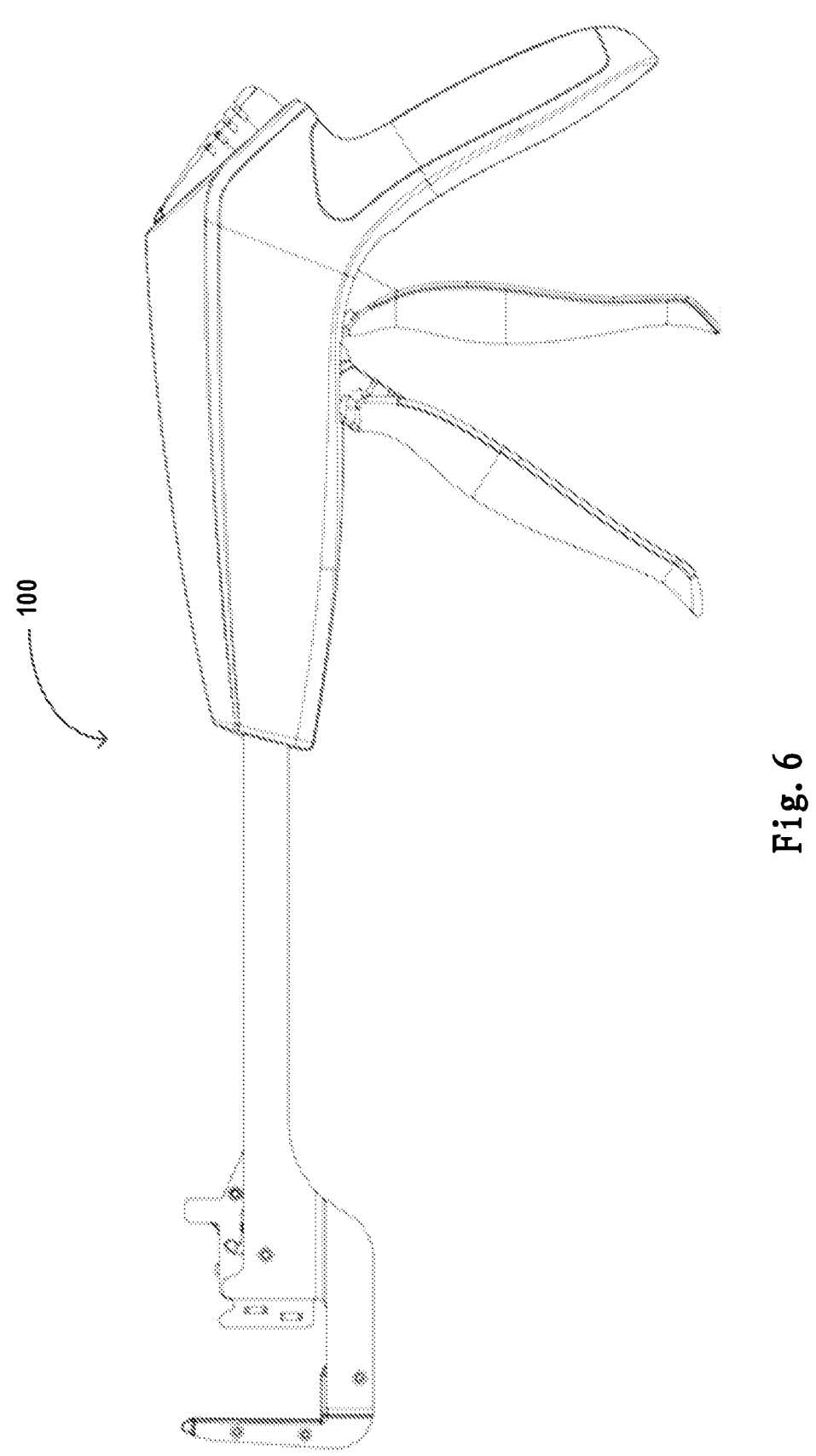
FIG. 6 exemplarily shows a surgical stapler without a surgical staple cartridge.
Figure 7:
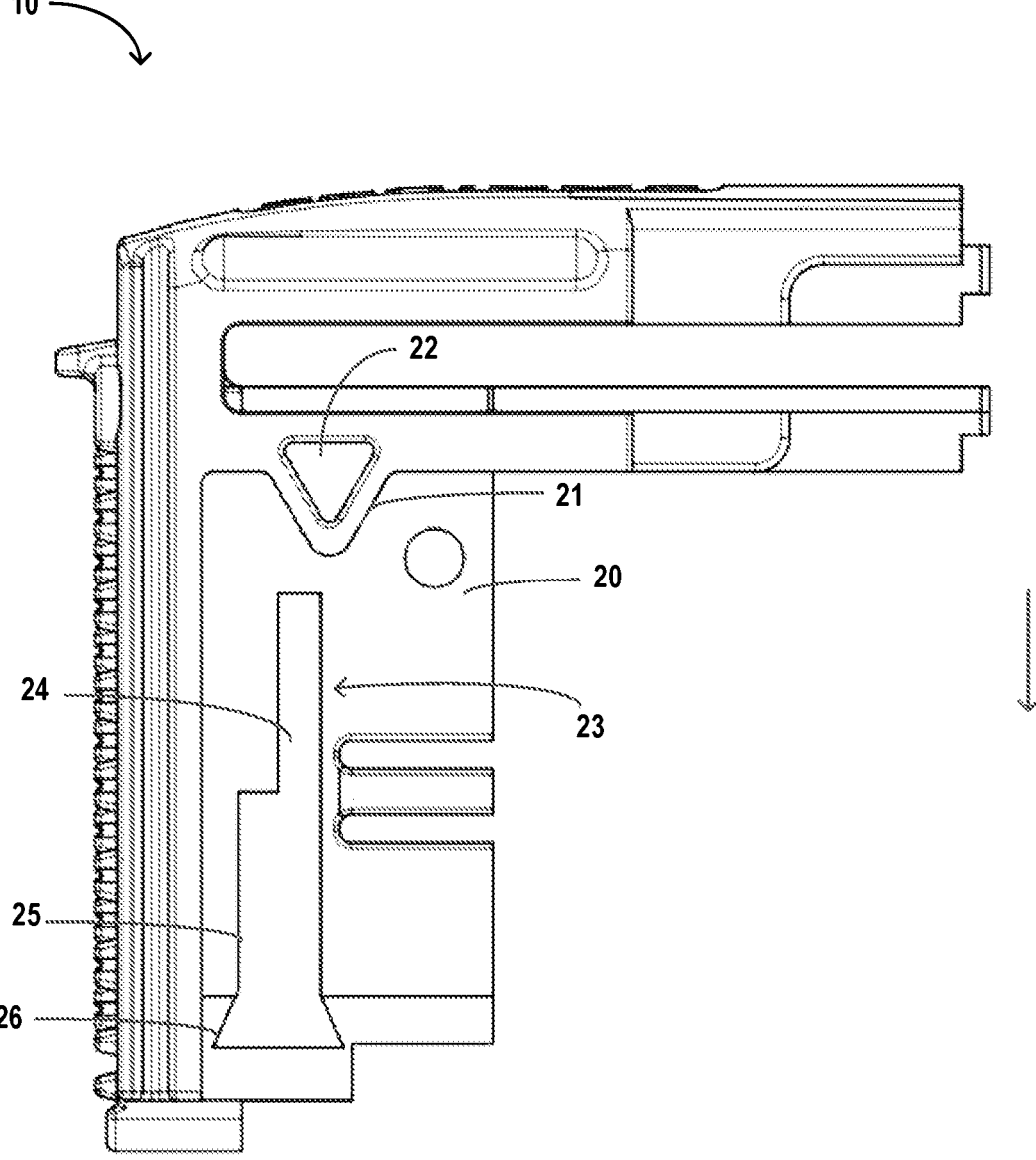
FIG. 7 exemplarily shows one side of a surgical staple cartridge according to a preferred embodiment of the present disclosure.
Figure 8:
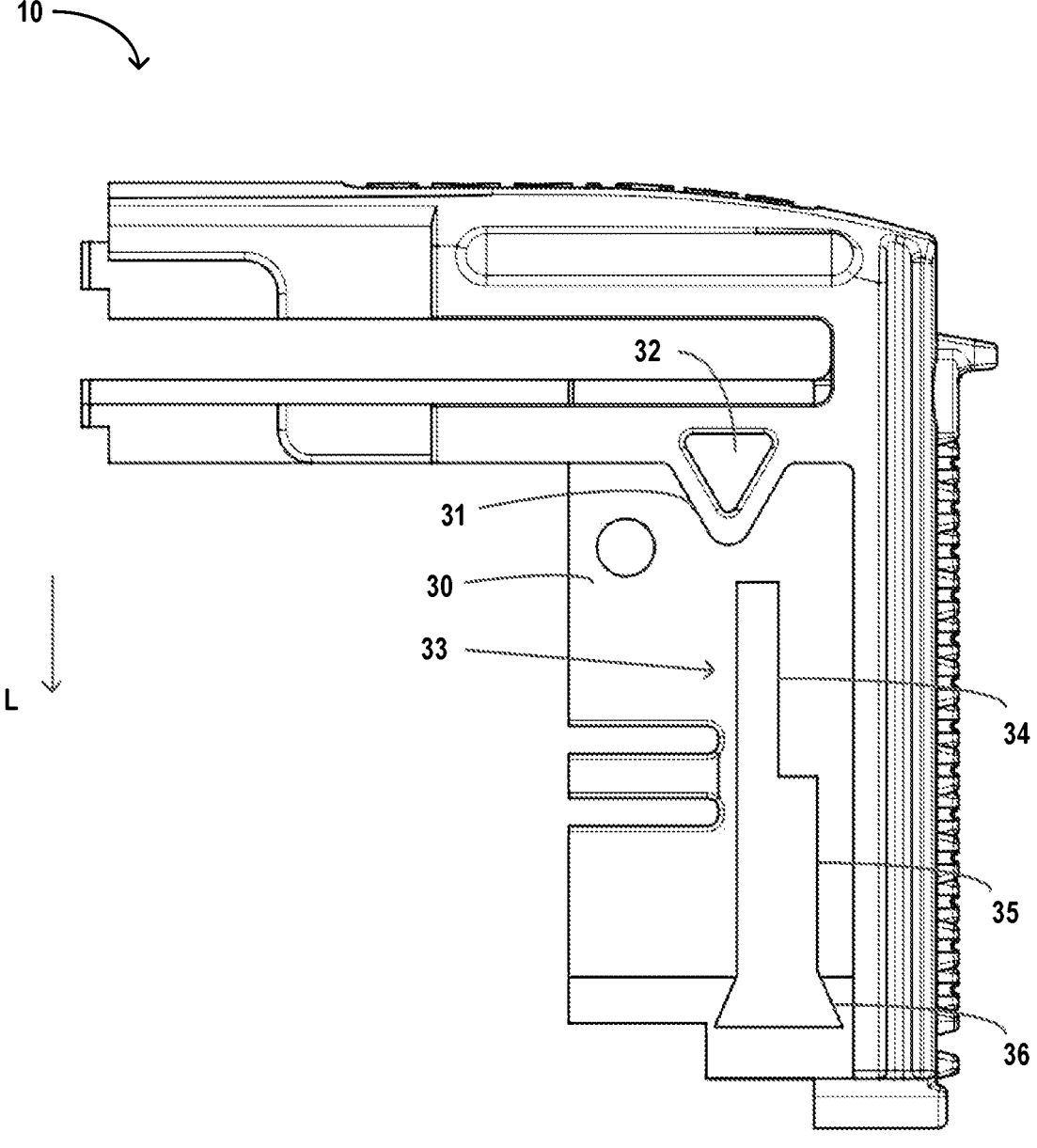
FIG. 8 exemplarily shows another side of the surgical staple cartridge shown in FIG. 7.

FIG. 6 exemplarily shows a surgical stapler 100 according to the present disclosure, FIG. 7 and FIG. 8 exemplarily show side views of both sides of a surgical staple cartridge 10 according to the present disclosure, wherein the surgical staple cartridge 10 can be removably installed in a surgical stapler like the surgical stapler 100 in FIG. 6.

As shown in FIG. 7, the surgical staple cartridge 10 comprises side walls 20, 30 extending along a longitudinal direction L (an installation direction of the staple cartridge in a surgical instrument), the side walls 20, 30 being arranged in parallel and opposite to each other. A first protrusion 21 is provided on an outer surface of the first side wall 20 at a position adjacent to a top end of the first side wall 20, the first protrusion 21 is used to match with a first notch 51 at a top end of a first closure plate 50 of the surgical instrument 100, in order to guide the surgical staple cartridge to be correctly installed while preventing an incorrect model of the surgical staple cartridge from being installed into the surgical instrument 100 (see FIG. 10 and FIG. 11).

Figure 12:
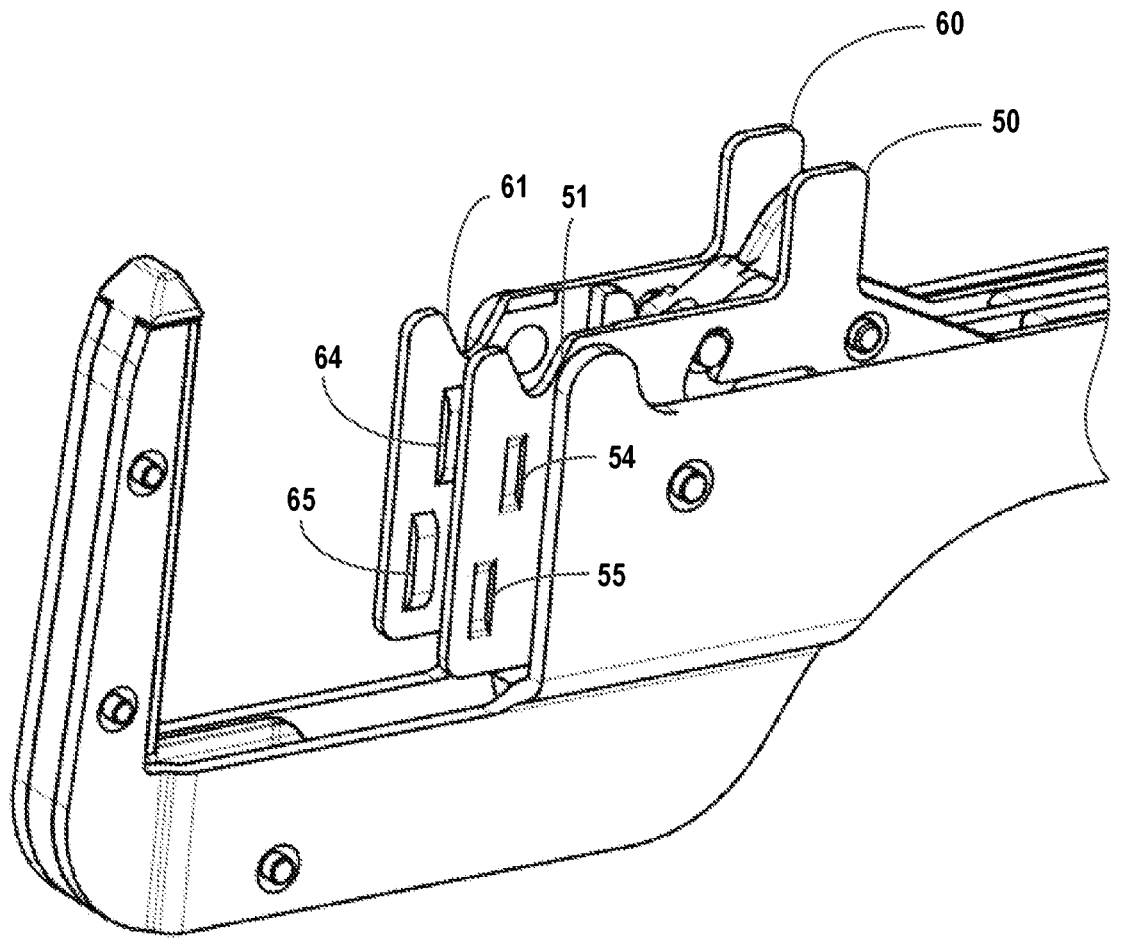
FIG. 12 exemplarily shows an enlarged perspective view of the end effector portion of the surgical stapler of FIG. 6.

As further shown in FIG. 8, a second protrusion 31 is provided on an outer surface of the second side wall 30 at a position adjacent to a top end of the second side wall 30, the second protrusion 31 is used to match with a second notch 61 at a top end of a second closure plate 60 of the surgical instrument, in order to guide the surgical staple cartridge to be correctly installed while preventing an incorrect model of surgical staple cartridge from being installed into the surgical instrument 100 (see FIG. 12).

It will be understood that in the staple cartridge of the present disclosure, it is not necessary to provide the protrusions in both side walls, and the purpose of the present disclosure may also be achieved by providing the protrusion on only one of the side walls.

Figure 9:
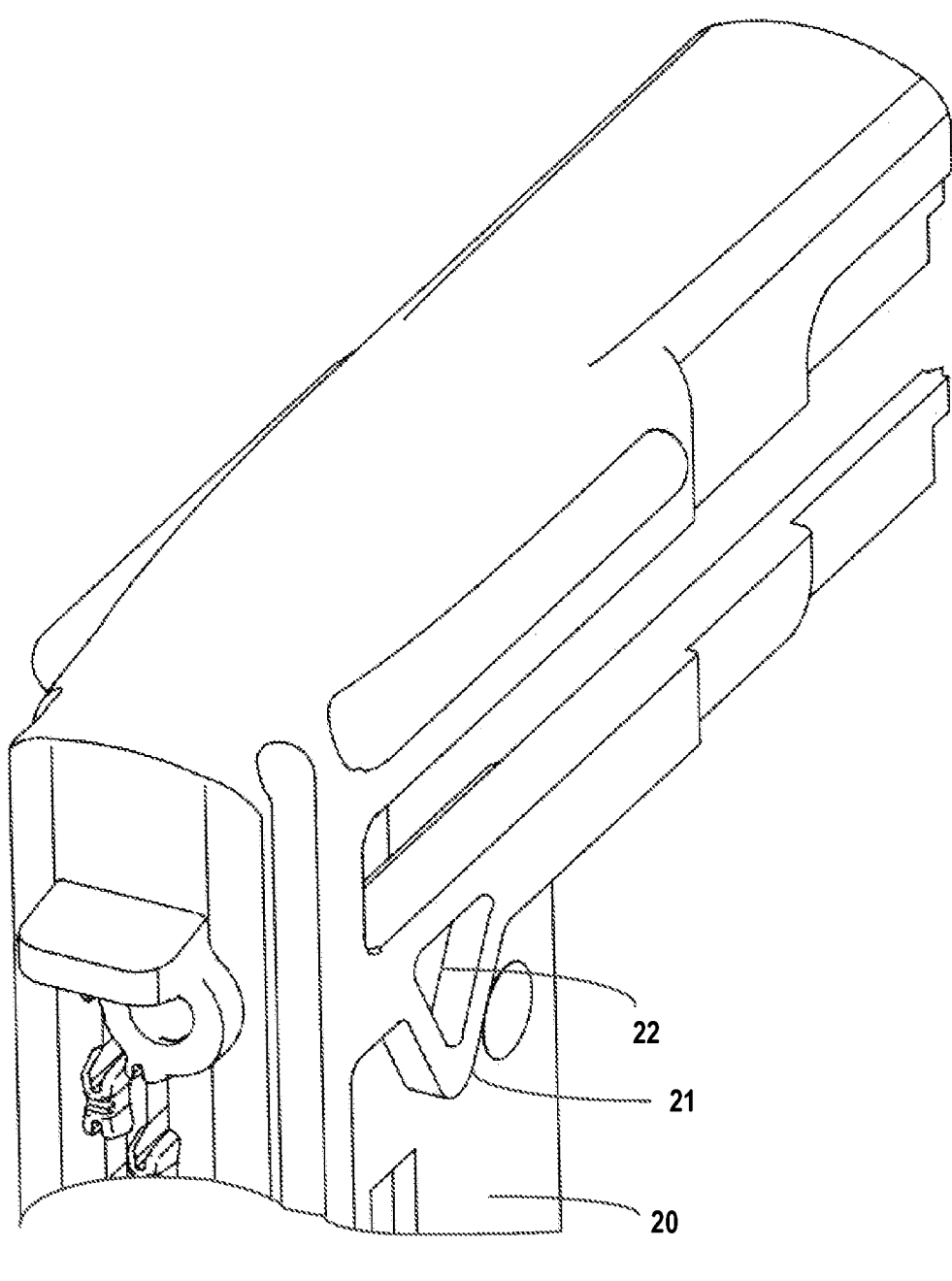
FIG. 9 exemplarily shows a perspective view of the surgical staple cartridge shown in FIG. 7.

The protrusions 21, 31 shown in the figures are of generally inverted triangular profiles, wherein a vertex of the triangular profile faces towards the installation direction of the staple cartridge, which is helpful to guide the staple cartridge to be correctly installed in the surgical instrument. As further shown in FIG. 9, the first protrusion 21 is further provided with a recess area 22 having substantially the same profile as that of the first protrusion 21, and the recess area 22 may be used to indicate the installation direction of the surgical staple cartridge. Therefore, the recess area 22 may have other profiles as long as it can indicate the installation direction of the surgical staple cartridge for the user. A similar recess area 32 is provided in the second protrusion 31.

According to the embodiments of the present disclosure, it is conceivable that the protrusions 21, 31 may also have other profiles, such as a substantially arc profile or trapezoidal profile, and a tapered end of the arc profile or trapezoidal profile is preferably oriented towards the installation direction of the surgical staple cartridge, so as to facilitate the guidance of the proper installation of the staple cartridge.

Figure 10:
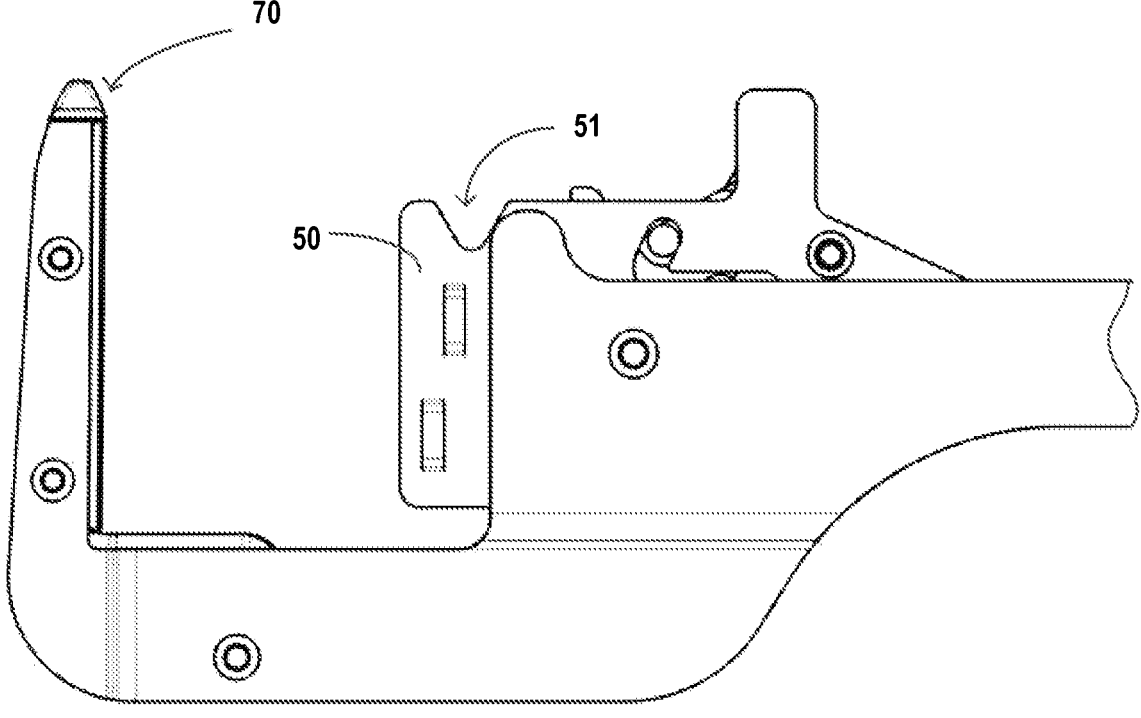
FIG. 10 exemplarily shows an enlarged view of an end effector portion of the surgical stapler shown in FIG. 6, wherein the surgical stapler is not equipped with a surgical staple cartridge.
Figure 11:
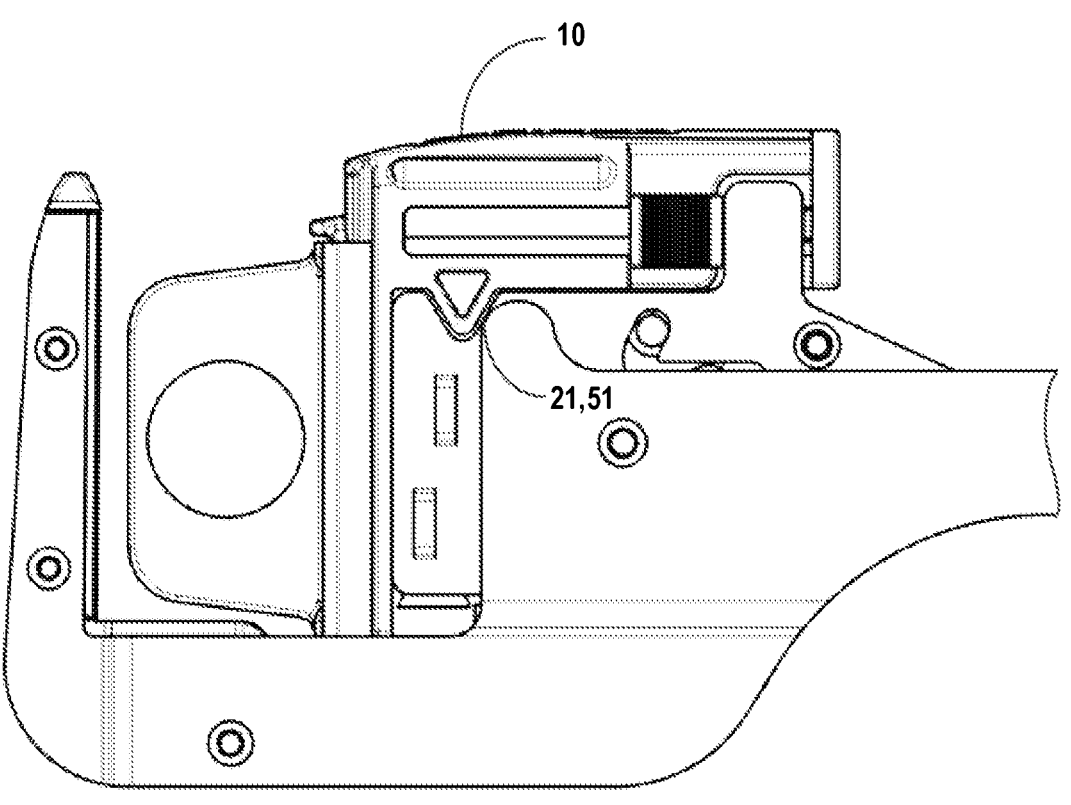
FIG. 11 exemplarily shows an enlarged view of the end effector portion of the surgical stapler shown in FIG. 6, wherein the surgical stapler is equipped with the surgical staple cartridge according to the present disclosure.

Referring to FIG. 10 and FIG. 12, the notches 51, 61 for receiving the protrusions 21, 31 are respectively provided on the top ends of the first closure plate 50 and the second closure plate 60 in the end effector of the surgical instrument 100. FIG. 11 shows a condition where the staple cartridge 10 is correctly installed in the surgical instrument, wherein the protrusions 21, 31 are respectively received in the notches 51, 61. As described above, although the notches 51, 61 shown in the figures have a generally triangular profile, the notches 51, 61 may also have other profiles as long as they can match with the profiles of the protrusions 51, 61.

It is conceivable that the protrusions 21, 31 may have different profiles from each other, and correspondingly, the notches 51, 61 may also have different profiles from each other.

Further, the surgical staple cartridge of the present disclosure may further comprise slots 23, 33 respectively provided on the outer surfaces of the side walls 20, 30. The slots 23, 33 are respectively positioned below the protrusions 22, 32, and extend along the installation direction L of the staple cartridge. The slot may cooperate with ribs on an inner side of the closure plate of the surgical instrument, which on one hand may be used to prevent the staple cartridge from being installed in an incompatible model of surgical instrument, and on the other hand, may be used to assist the closure plate to push the staple cartridge.

As shown in FIG. 7 and FIG. 8, the slot 23 comprises two portions 24 and 25, wherein the slot 25 is wider than the slot 24 and one side of the slot 25 is aligned with the same side of the slot 24. Similarly, the slot 33 comprises two portions 34 and 35, wherein the slot 35 is wider than the slot 34 and one side of the slot 35 is aligned with the same side of the slot 34. Correspondingly, the inner sides of the closure plates 50, 60 of the surgical instrument 100 are respectively provided with two ribs or two rows of ribs extending along the installation direction L (a longitudinal direction) of the staple cartridge and mutually staggered along a driving direction (a lateral direction) of the closure plates. As shown in the figures, an inner surface of the closure plate 50 is provided with ribs 54, 55 which are laterally offset from each other, and an inner surface of the closure plate 60 is provided with ribs 64, 65 which are laterally offset from each other. When the surgical staple cartridge is installed between the closure plate 50 and the closure plate 60 along the installation direction L, the slot 24 receives the rib 54, and the slot 25 receives the rib 55 which is laterally offset relative to the rib 54, and similarly, on the other side, the slot 34 receives the rib 64, and the slot 35 receives the rib 65 which is laterally offset relative to the rib 64, thereby enabling the staple cartridge to be installed in place on the surgical instrument. It will be understood by those skilled in the art that although only one rib 54, 55, 64, 65 is shown in the figures, more than one ribs 54, 55 arranged in rows may be provided on the inner surface of the closure plate 50, and more than one ribs 64, 65 arranged in rows may also be provided on the inner surface of the closure plate 60.

Figure 13:
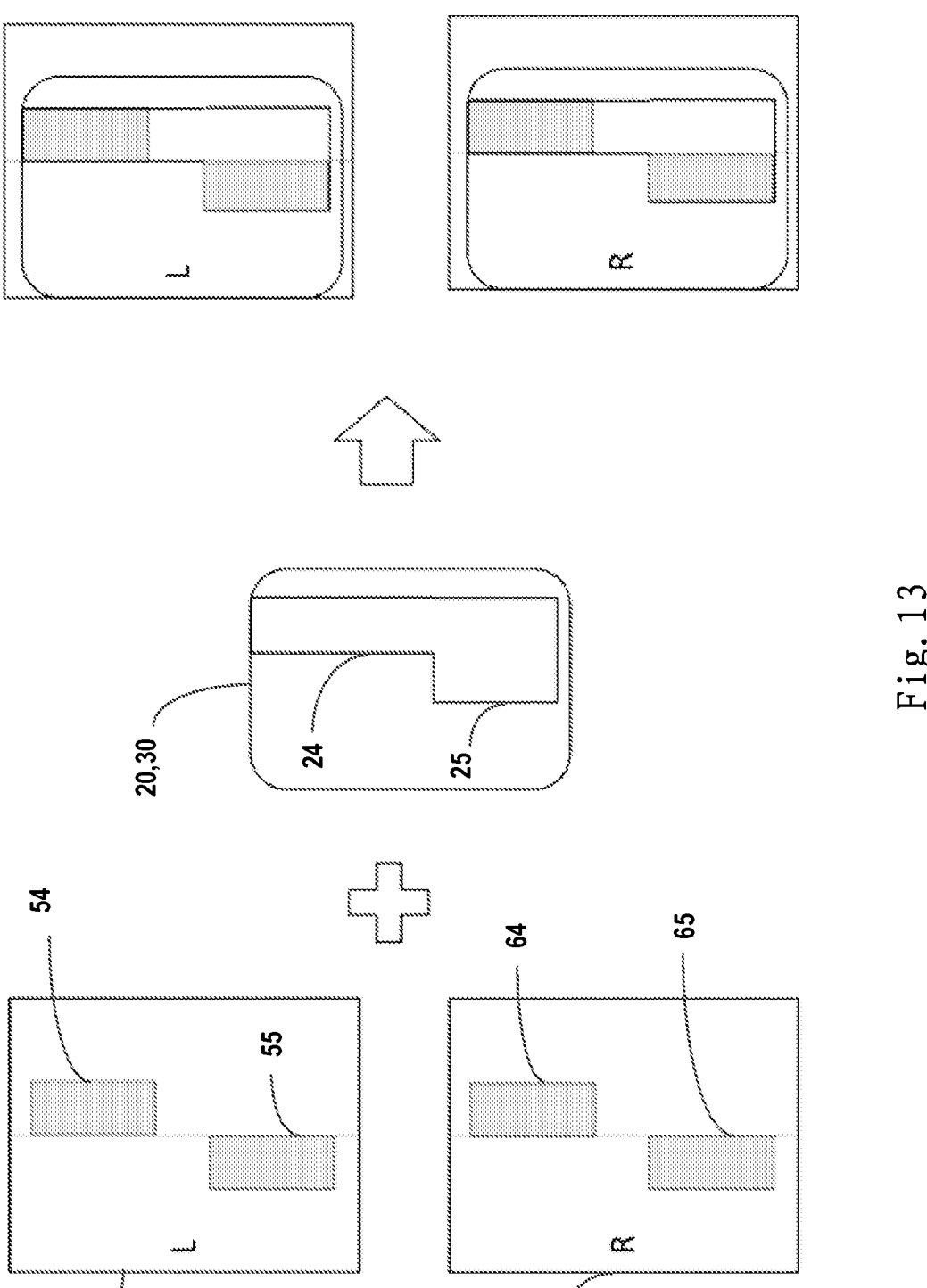
FIG. 13 exemplarily shows the cooperation between the surgical staple cartridge of the present disclosure and a compatible surgical instrument.

FIG. 13 exemplarily shows the cooperation between the surgical staple cartridge according to the present disclosure and a compatible surgical instrument. When the staple cartridge is installed along the installation direction L, the rib 54 firstly slides through the slot portion 25 and then slides into the slot portion 24, and the rib 55 which is laterally staggered with the rib 54 slides into a laterally offset portion of the slot portion 25; and on the other side, the rib 64 firstly slides through the slot portion 35 and then slides into the slot portion 34, and the rib 65 which is laterally staggered with the rib 64 slides into a laterally offset portion of the slot portion 35.

In a further preferred embodiment, as shown in FIG. 7 and FIG. 8, open tip ends of the slots 25, 35 may further have funnel-shaped flared sections 26, 36 to assist the alignment of the slots with the ribs, so as to facilitate the installation of the staple cartridge.

After the surgical staple cartridge 10 has been correctly installed between a pair of the closure plates 50, 60 of the surgical instrument 100, the surgical staple cartridge 10 may be moved towards the staple anvil portion 70 (see FIG. 10) of the surgical instrument under the pushing of the closure plates, so as to clamp tissue between the surgical staple cartridge and the staple anvil portion for subsequent stapling and cutting operations.

It will be understood that in the staple cartridge of the present disclosure, it is not necessary to provide the slots 23, 33 in both side walls 20, 30, and the purpose of the present disclosure can also be achieved by providing the slot in only one side wall. In addition, a shape of the slot 23 may also be different from that the slot 33, or they can be asymmetrically arranged.

Figure 14:
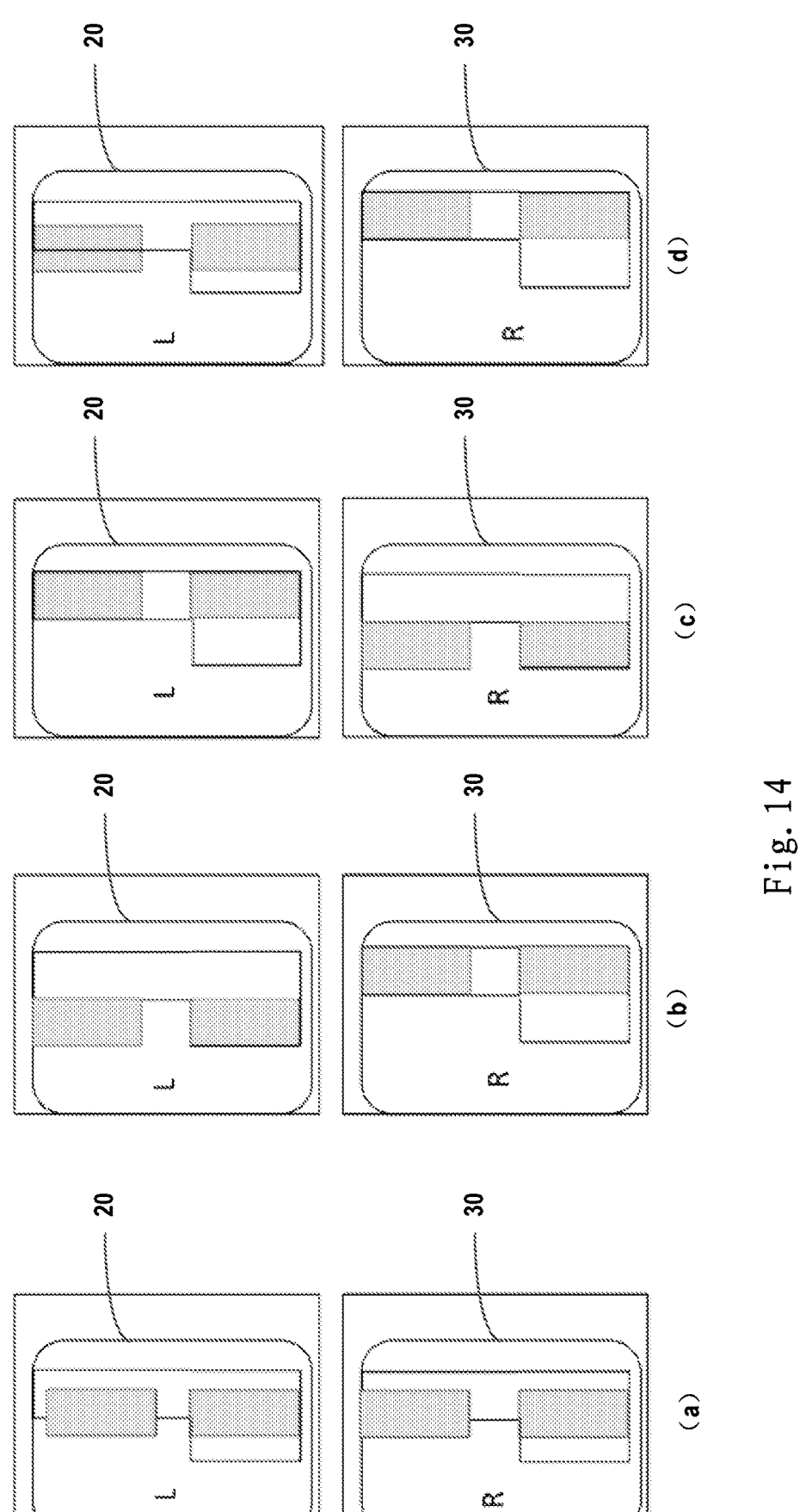
FIG. 14 exemplarily shows the interference between the surgical staple cartridge of the present disclosure and incompatible surgical instruments.

FIG. 14 exemplarily shows that the staple cartridge according to the present disclosure is installed in incompatible surgical instruments, wherein L indicates a left side wall of the staple cartridge and left closure plates of surgical instruments, and R indicates a right side wall of the staple cartridge and right closure plates of surgical instruments. In Example (a) of FIG. 14, an upper rib on the left closure plate of an incompatible surgical instrument is incapable of being received in a slot on the left side wall 20 of the staple cartridge of the present disclosure, and an upper rib on the right closure plate of the incompatible surgical instrument is incapable of being received in a slot on the right side wall 30 of the staple cartridge of the present disclosure; in Example (b), neither the upper rib nor the lower rib of the left closure plate of an incompatible surgical instrument is capable of being received in the slot of the left side wall 20 of the staple cartridge of the present disclosure; In Example (c), neither the upper rib nor the lower rib of the right closure plate of an incompatible surgical instrument is capable of being received in the slot of the right side wall 30 of the staple cartridge of the present disclosure; In Example (d), the upper rib of the left closure plate of an incompatible surgical instrument is incapable of being received in the slot of the left side wall 20 of the staple cartridge of the present disclosure. Due to the above-mentioned various interferences, the surgical staple cartridge according to the present disclosure is incapable of being installed in incompatible surgical instruments.

Figure 15:
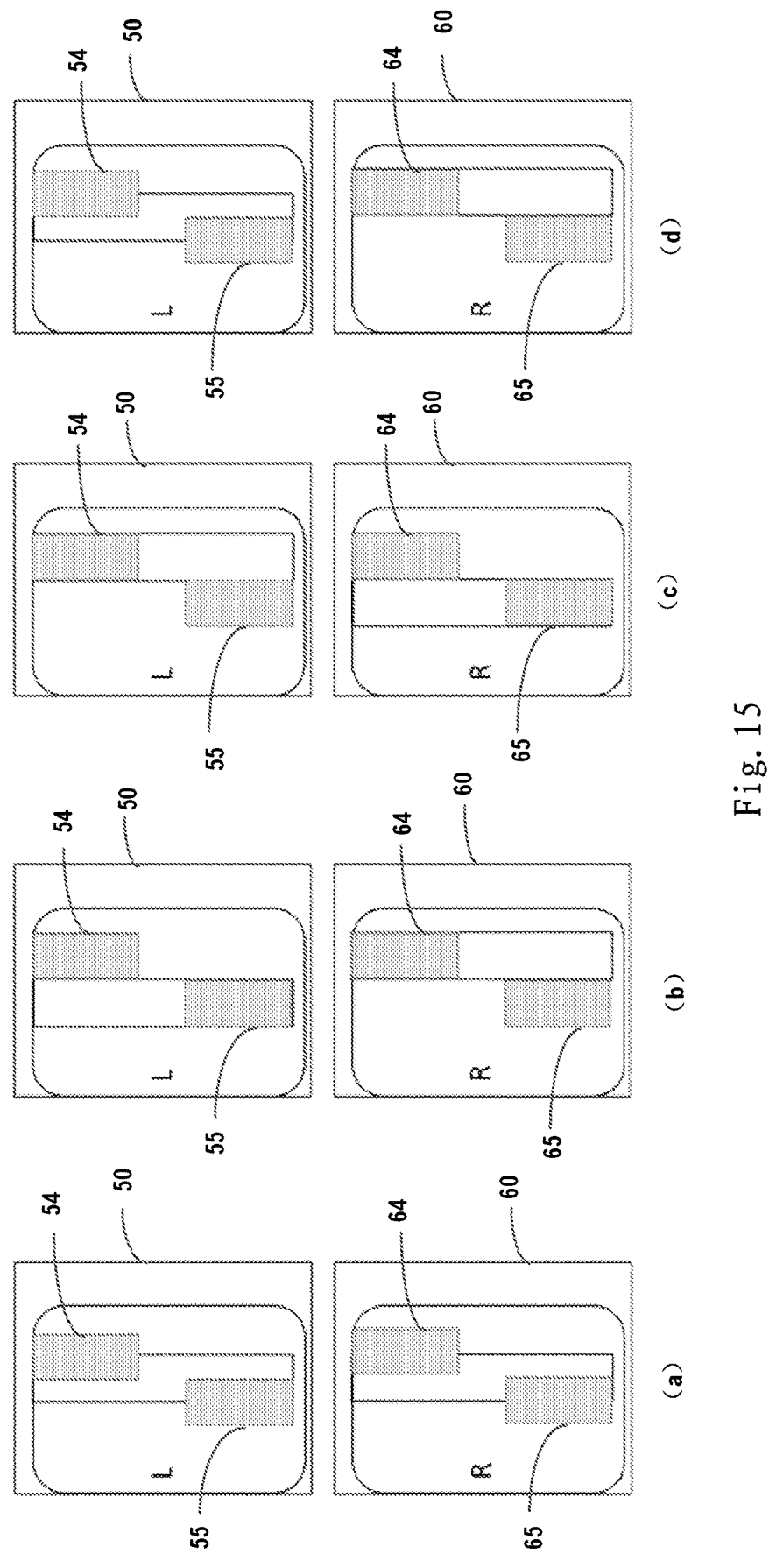
FIG. 15 exemplarily shows the interference between a surgical instrument which is compatible with the surgical staple cartridge of the present disclosure and other existing surgical staple cartridges.

FIG. 15 exemplarily shows the interference between a surgical instrument which is compatible with the surgical staple cartridge of the present disclosure and other existing surgical staple cartridges, wherein L indicates left side walls of staple cartridges and a left closure plate of the surgical instrument, and R indicates right side walls of staple cartridges and a right closure plate of the surgical instrument. As shown in the figure, slots on the left side walls and the right side walls of the existing surgical staple cartridges are constant in width along their lengths. In Example (a) of FIG. 15, all ribs on the left closure plate 50 and the right closure plate 60 of the surgical instrument is incapable of being received in slots of an incompatible surgical staple cartridge; in Example (b), an upper rib 54 of the left closure plate 50 of the surgical instrument is incapable of being received in a slot of an incompatible surgical staple cartridge, and an lower rib 65 of the right closure plate 60 is incapable of being received in a slot of the incompatible surgical staple cartridge; in Example (c), an lower rib 55 of the left closure plate 50 of the surgical instrument is incapable of being received in a slot of an incompatible surgical staple cartridge, and an upper rib 64 of the right closure plate 60 is incapable of being received in a slot of the incompatible surgical staple cartridge; in Example (d), neither the upper rib 54 nor the lower rib 55 of the left closure plate 60 of the surgical instrument is capable of being received in a slot of the incompatible surgical staple cartridge, and the lower rib 65 of the right closure plate 60 is incapable of being received in the slot of an incompatible surgical staple cartridge. Due to the above-mentioned interference, the surgical instrument compatible with the surgical staple cartridge of the present disclosure will not be able to be installed with other existing surgical staple cartridges.

Figure 16:
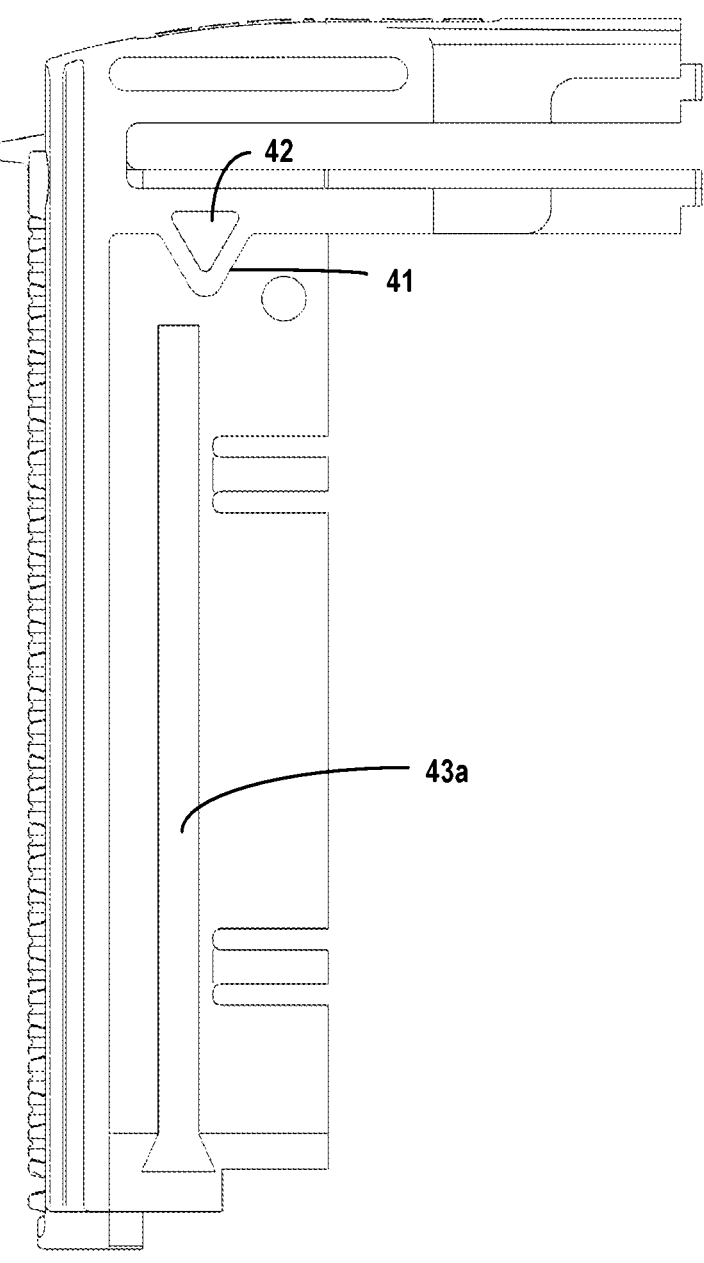
FIG. 16 exemplarily shows a side view of one side of a surgical staple cartridge according to another preferred embodiment of the present disclosure.
Figure 17:
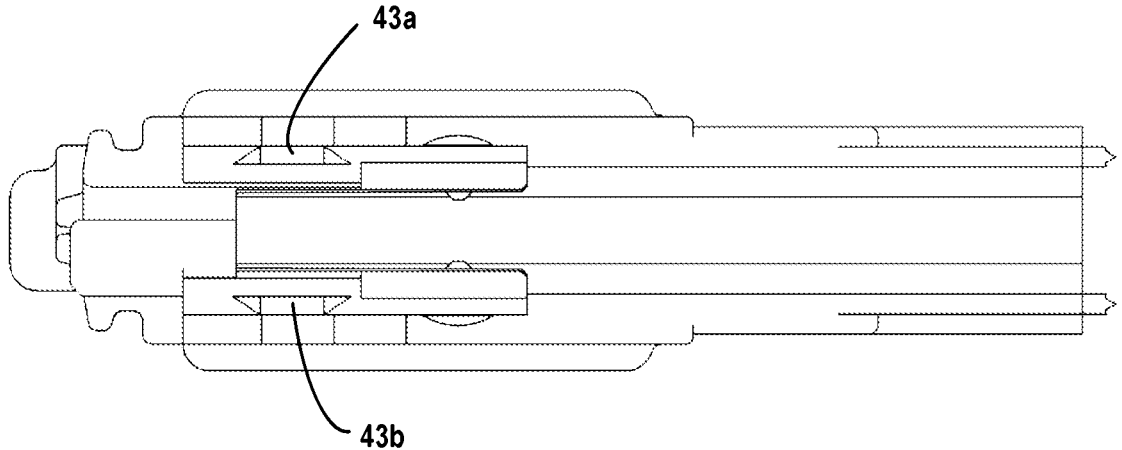
FIG. 17 exemplarily shows a bottom view of the surgical staple cartridge shown in FIG. 16.

FIG. 16 and FIG. 17 exemplarily show a surgical staple cartridge according to another preferred embodiment of the present disclosure. Similar to the surgical staple cartridge shown in FIGS. 7 to 9, the surgical staple cartridge shown in FIG. 16 also comprises: a protrusion 41 provided on at least one side wall for cooperating with a notch at a top end of a closure plate of a surgical instrument to guide the surgical staple cartridge to be correctly installed while preventing an incorrect model of surgical staple cartridge from being installed in the surgical instrument; a recess area 22 for indicating an installation direction of the surgical staple cartridge; and slots 43a, 43b positioned on outer surfaces of at least one side wall of the staple cartridge, the slots 43a, 43b being configured to cooperate with ribs on inner sides of the closure plates of the surgical instrument, which on one hand may be used to prevent the staple cartridge from being installed in an incompatible model of surgical instrument, and on the other hand, may be used to assist the closure plates to push the staple cartridge. As compared to the surgical staple cartridge shown in FIGS. 7 to 9, the difference is that the width of the slots 43a, 43b is constant along their length, except for flared sections at tip ends of the slots 43a, 43b. The slot 43a or the slot 43b is used to receive only one rib or one row of ribs on the inner side the closure plate of the surgical instrument, rather than receive multiple ribs or multiple rows of ribs arranged in a staggered manner. FIG. 17 shows the slots 43*a*, 43*b* being symmetrically arranged on both sides of the surgical staple cartridge. Of course, as mentioned above, the slots 43*a*, 43*b* may also be asymmetrically arranged on the lateral sides of the surgical staple cartridge.

Figure 18:
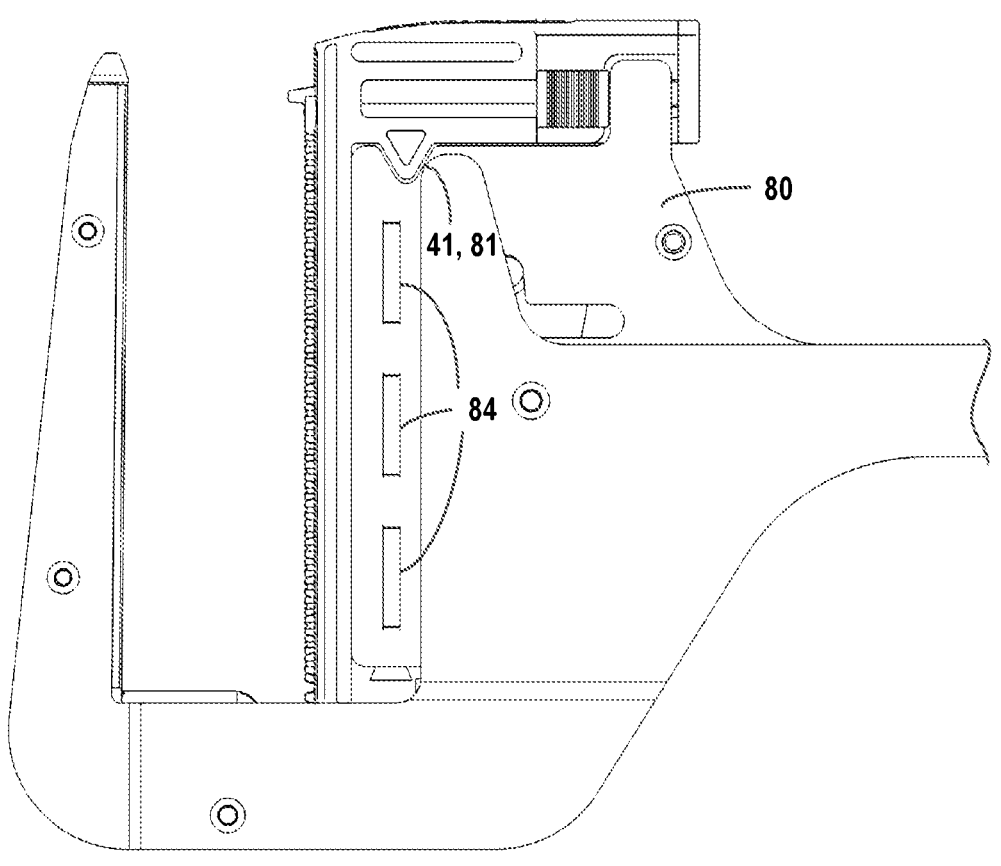
FIG. 18 exemplarily shows an enlarged view of an end effector portion of a surgical instrument which is compatible with the surgical staple cartridge shown in FIG. 16, wherein the surgical instrument is equipped with the surgical staple cartridge shown in FIG. 16.

FIG. 18 exemplarily shows an enlarged view of an end effector portion of a surgical instrument which is compatible with the surgical staple cartridge shown in FIG. 16, wherein the surgical instrument is installed with the surgical staple cartridge of FIG. 16. As shown in the figure, the protrusion 41 of the surgical staple cartridge is accommodated in a notch 81 at a top end of a closure plate 80 of the surgical instrument, and the slot 43*a* slidably receives a row of ribs 84. Those skilled in the art will understand that although three ribs 84 are shown in the figure, one, two or more than three ribs 84 may also be possible.

The scope of protection of the present disclosure is defined only by the claims. References in this specification to "various embodiments", "some embodiments", "one embodiment" or "an embodiment" mean that specific features, structures or characteristics described in conjunction with the embodiments are included in at least one embodiment. Therefore, the phrases "in various embodiments", "in some embodiments", "in one embodiment" or "in an embodiment" and the like in the present specification are not necessarily all referring to the same embodiment. Furthermore, in one or more embodiments, the specific features, structures or characteristics may be combined in any suitable way. Therefore, without conflict, the specific features, structures or characteristics shown or described in conjunction with one embodiment can be fully or partially combined with the features, structures or characteristics of one or more other embodiments, and the resulting modifications and variations are also within the scope of the present disclosure.

We claim:

1. A surgical staple cartridge configured to be removably installed between a pair of closure plates of a surgical instrument, the pair of closure plates including a first closure plate and a second closure plate, the pair of closure plates being configured to push the surgical staple cartridge towards a staple anvil portion of the surgical instrument to clamp tissue between the surgical staple cartridge and the staple anvil portion, the surgical staple cartridge comprising:
    a first side wall extending along a longitudinal direction parallel to an installation direction of the surgical staple cartridge, with a first protrusion being provided on an outer surface of the first side wall at a position adjacent to a top end of the first side wall; and
    a second side wall arranged in parallel and opposite to the first side wall;
    wherein the first protrusion is configured to match with a first notch at a top end of the first closure plate to guide the surgical staple cartridge to be correctly installed;
    wherein the first protrusion includes a planar surface configured to contact the first notch.

2. The surgical staple cartridge according to claim 1, wherein the first protrusion has a substantially triangular profile, and wherein a vertex of the triangular profile faces towards the installation direction of the surgical staple cartridge.

3. The surgical staple cartridge according to claim 1, wherein the first protrusion has a substantially arc profile or trapezoidal profile, and wherein a tapered end of the arc profile or the trapezoidal profile faces towards the installation direction of the surgical staple cartridge.

4. The surgical staple cartridge according to claim 1, wherein the first protrusion includes a recess area, and wherein a profile of the recess area is configured to indicate the installation direction of the surgical staple cartridge.

5. The surgical staple cartridge according to claim 4, wherein the profile of the recess area is substantially the same as a profile of the first protrusion.

6. The surgical staple cartridge according to claim 1, wherein an outer surface of the second side wall includes a second protrusion at a position adjacent to a top end of the second side wall, and wherein the second protrusion is configured to match with a second notch at a top end of the second closure plate of the surgical instrument to guide the surgical staple cartridge to be correctly installed.

7. The surgical staple cartridge according to claim 6, wherein the second protrusion has a substantially triangular profile, and wherein a vertex of the triangular profile faces towards the installation direction of the surgical staple cartridge.

8. The surgical staple cartridge according to claim 6, wherein the second protrusion has a substantially arc profile or trapezoidal profile, and wherein a tapered end of the arc profile or the trapezoidal profile faces towards the installation direction of the surgical staple cartridge.

9. The surgical staple cartridge according to claim 6, wherein the second protrusion includes a recess area, and wherein a profile of the recess area is configured to indicate the installation direction of the surgical staple cartridge.

10. The surgical staple cartridge according to claim 9, wherein the profile of the recess area is substantially the same as a profile of the second protrusion.

11. The surgical staple cartridge according to claim 1, wherein the outer surface of the first side wall includes a first slot extending in the longitudinal direction, and wherein the first slot is configured to receive one or more ribs of an inner surface of the first closure plate.

12. The surgical staple cartridge according to claim 11, wherein a the outer surface of the second side wall includes second slot extending in the longitudinal direction, and wherein the second slot is configured to receive one or more ribs of an inner surface of the second closure plate.

13. The surgical staple cartridge according to claim 12, wherein the first slot and the second slot are asymmetrically arranged on lateral sides of the surgical staple cartridge.

14. The surgical staple cartridge according to claim 1, wherein the outer surface of the first side wall includes a first slot extending in the longitudinal direction, and wherein the first slot includes a first partial slot adjacent to the top end of the first side wall and a second partial slot adjacent to a bottom end of the first side wall, the second partial slot being wider than the first partial slot.

15. The surgical staple cartridge according to claim 14, wherein a side of the second partial slot is aligned with a same side of the first partial slot, and when the surgical staple cartridge is installed between the first closure plate and the second closure plate along the installation direction, the first partial slot is configured to receive one or more first ribs provided on an inner surface of the first closure plate, and the second partial slot is configured to receive one or more second ribs provided on the inner surface of the first closure plate, the one or more second ribs being staggered from the one or more first ribs.

16. The surgical staple cartridge according to claim 14, wherein the first slot further comprises a flared section located at a bottom end of the second partial slot.

17. The surgical staple cartridge according to claim 14, wherein a the outer surface of the second side wall includes second slot extending in the longitudinal direction, and wherein the second slot includes a third partial slot adjacent to the top end of the second side wall and a fourth partial slot adjacent to a bottom end of the second side wall, the fourth partial slot being wider than the third partial slot.

18. The surgical staple cartridge according to claim 17, wherein a side of the fourth partial slot is aligned with a same side of the third partial slot, and when the surgical staple cartridge is installed between the first closure plate and the second closure plate along the installation direction, the third partial slot is configured to receive one or more third ribs provided on an inner surface of the second closure plate, and the fourth partial slot is configured to receive one or more fourth ribs provided on the inner surface of the second closure plate, the one or more fourth ribs being staggered from the one or more third ribs.

19. A closure member for a surgical instrument, the closure member being configured to removably hold a surgical staple cartridge and push the surgical staple cartridge towards a staple anvil portion of the surgical instrument to clamp tissue between the surgical staple cartridge and the staple anvil portion, the closure member comprising:
    a first closure plate; and
    a second closure plate arranged opposite to the first closure plate;
    wherein the surgical staple cartridge is configured to be removably installed between the first closure plate and the second closure plate, wherein a top end of the first closure plate includes a first notch for receiving a first protrusion on a first side wall of the surgical staple cartridge, and wherein the first notch includes a planar surface for contacting the first protrusion.

20. A closure member for a surgical instrument, the closure member being configured to removably hold a surgical staple cartridge and push the surgical staple cartridge towards a staple anvil portion of the surgical instrument to clamp tissue between the surgical staple cartridge and the staple anvil portion, the closure member comprising:
    a first closure plate; and
    a second closure plate arranged opposite to the first closure plate;
    wherein the surgical staple cartridge is configured to be removably installed between the first closure plate and the second closure plate, and wherein a top end of the first closure plate includes a first notch for receiving a first protrusion on a first side wall of the surgical staple cartridge, and
    wherein the top end of the first closure plate or a top end of the second closure plate includes a second notch for receiving a second protrusion on either the first side wall or a second side wall of the surgical staple cartridge.

\* \* \* \* \*